United States Patent
Shimizu et al.

(10) Patent No.: US 7,015,363 B2
(45) Date of Patent: Mar. 21, 2006

(54) PROCESS FOR PRODUCING ETHER COMPOUND

(75) Inventors: Ikuo Shimizu, Yokkaichi (JP); Katsuhiro Ito, Yokkaichi (JP); Kazuyasu Osada, Yokkaichi (JP); Tsuguo Yamaoka, Funabashi (JP)

(73) Assignee: Kyowa Yuka Co., Ltd., Tokyo (JP)

( * ) Notice: Subject to any disclaimer, the term of this patent is extended or adjusted under 35 U.S.C. 154(b) by 33 days.

(21) Appl. No.: 10/482,111

(22) PCT Filed: Jul. 12, 2002

(86) PCT No.: PCT/JP02/07117

§ 371 (c)(1), (2), (4) Date: Dec. 24, 2003

(87) PCT Pub. No.: WO03/006407

PCT Pub. Date: Jan. 23, 2003

(65) Prior Publication Data

US 2004/0181097 A1 Sep. 16, 2004

(30) Foreign Application Priority Data

Jul. 13, 2001 (JP) .............................. 2001-213246

(51) Int. Cl.
*C07C 41/54* (2006.01)
(52) U.S. Cl. ...................... 568/591; 568/592; 568/594; 568/605
(58) Field of Classification Search ................ 568/591, 568/592, 594, 605
See application file for complete search history.

(56) References Cited

U.S. PATENT DOCUMENTS 3,294,781 A * 12/1966 Ollidene et al. ............. 536/111
4,841,075 A * 6/1989 Matsushita et al. ......... 549/341
6,159,653 A * 12/2000 Malik et al. ............. 430/270.1

FOREIGN PATENT DOCUMENTS

| DE | 43 38 394 | | 5/1995 |
| EP | 1 050 523 | | 11/2000 |
| JP | 07-069955 | * | 3/1995 |
| JP | 2000-298344 | | 10/2000 |

OTHER PUBLICATIONS

Y. Nakane, et al., "Hemiacetal Esterification of Methacrylic Acid", *Journal of the Adhesion Society of Japan*, vol. 34, No. 7 (1998).

* cited by examiner

Primary Examiner—Rosalynd Keys
(74) Attorney, Agent, or Firm—Fitzpatrick, Cella, Harper & Scinto

(57) ABSTRACT

The present invention provides the following process for producing and the like, which enables the production of an ether compound, which is useful for chemical amplification type resist compositions, synthetic intermediates of pharmaceuticals, paints, or the like, with less side reaction and in high yield.

A process for producing an ether compound having a group represented by the general formula (II)

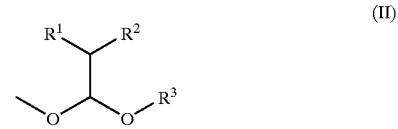

(II)

wherein $R^1$, $R^2$ and $R^3$ may be the same or different, and represent substituted or unsubstituted alkyl, substituted or unsubstituted aryl or substituted or unsubstituted aralkyl, or $R^1$ and $R^2$ form cycloalkyl together with an adjacent carbon atom, which comprises allowing a compound having a hydroxyl group (including a carboxyl group) to react with an alkenyl ether represented by the general formula (I)

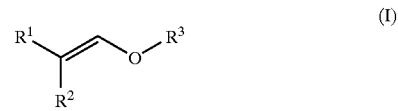

(I)

wherein $R^1$, $R^2$ and $R^3$ have the same significances as defined above, respectively.

3 Claims, No Drawings

PROCESS FOR PRODUCING ETHER COMPOUND

TECHNICAL FIELD

The present invention relates to a process for producing an ether compound which is useful for chemical amplification type resist compositions, synthetic intermediates of pharmaceuticals, paints, or the like; a protective agent of a hydroxyl group, which can give a compound with a hydroxyl group protected; and the like.

BACKGROUND ART

Hemiacetal esters and acetals derived from an alkyl vinyl ether are useful for chemical amplification type resist compositions, synthetic intermediates of pharmaceuticals, paints, or the like, because leaving of a group derived from the alkyl vinyl ether by heat, an acid catalyst or the like easily occurs. For example, use of hemiacetal esters and acetals, which are derived from an alkyl vinyl ether, in a chemical amplification type resist composition has been known (Japanese Published Unexamined Patent Application No. 2000-298344 and the like). Hemiacetal esters and acetals derived from an alkyl vinyl ether are generally produced by allowing of an alkyl vinyl ether to react with a compound having a carboxyl group or the like in the presence of an acid catalyst or the like. However, for example, when an ethyl vinyl ether or the like is allowed to react with a compound having a carboxyl group or the like, there has been a problem that a byproduct such as a polymer of the ethyl vinyl ether or the like is produced. In addition, when a polymer comprising a carboxyl group, which has been subjected to hemiacetal esterification using an ethyl vinyl ether, is used in a chemical amplification type resist composition, stability of the hemiacetal ester is inferior in a prebaking step conducted for the purpose of removing an organic solvent used upon spin coating of the polymer on a silicon wafer, or during storage for a long period of time. Thus, the polymer was also unsatisfactory for practical use.

Further, synthesis of a hemiacetal ester was studied in Journal of Adhesion Society of Japan, vol. 34, p. 246 (1998), in which a reaction between a straight chain alkyl vinyl ether and a compound having a carboxyl group was performed in the presence of various kinds of acids. However, in the presence of an acid other than phosphoric acid (hydrochloric acid, sulfuric acid, nitric acid), the result was that the yield was low and a large number of polymers, which are byproducts, derived from the alkyl vinyl ether was produced.

DISCLOSURE OF THE INVENTION

An object of the present invention is to provide a process for producing an ether compound, which is useful for chemical amplification type resist compositions, synthetic intermediates of pharmaceuticals, paints, or the like, with less side reaction and in a high yield; a protective agent of a hydroxyl group, which can give a compound with a hydroxyl group protected that is excellent in thermostability; or the like.

The present invention provides the following [1] to [9].

[1] A process for producing an ether compound having a group represented by the general formula (II)

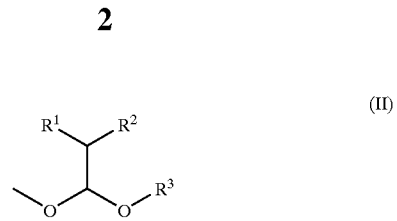

wherein $R^1$, $R^2$ and $R^3$ may be the same or different, and represent substituted or unsubstituted alkyl, substituted or unsubstituted aryl or substituted or unsubstituted aralkyl, or $R^1$ and $R^2$ form cycloalkyl together with an adjacent carbon atom, which comprises allowing a compound having a hydroxyl group (including a carboxyl group, the same also applies hereinafter) to react with an alkenyl ether represented by the general formula (I)

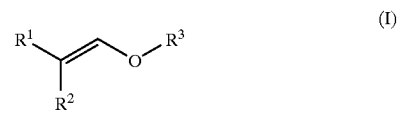

wherein $R^1$, $R^2$ and $R^3$ have the same significances as defined above, respectively.

[2] A process for producing an ether compound having a group represented by the general formula (IIa)

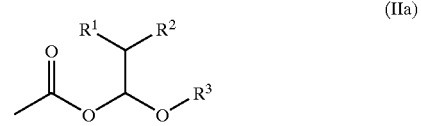

wherein $R^1$, $R^2$ and $R^3$ have the same significances as defined above, respectively, which comprises allowing a compound having a carboxyl group to react with an alkenyl ether represented by the general formula (I)

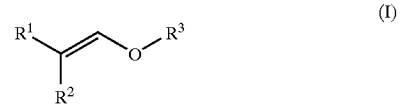

wherein $R^1$, $R^2$ and $R^3$ have the same significances as defined above, respectively.

[3] The process for producing according to the above [1] or [2] wherein the reaction is conducted in the presence of an acid catalyst.

[4] A process for protecting a hydroxyl group which comprises allowing a compound having a hydroxyl group to react with an alkenyl ether represented by the general formula (I)

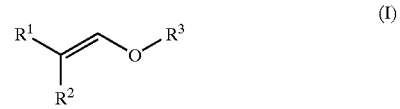

wherein R¹, R² and R³ have the same significances as defined above, respectively, to lead to an ether compound having a group represented by the general formula (II)

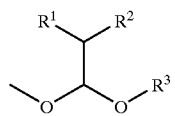

(II)

wherein R¹, R² and R³ have the same significances as defined above, respectively.

[5] A process for protecting a carboxyl group which comprises allowing a compound having a carboxyl group to react with an alkenyl ether represented by the general formula (I)

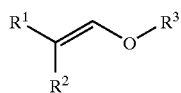

(I)

wherein R¹, R² and R³ have the same significances as defined above, respectively, to lead an ether compound having a group represented by the general formula (IIa)

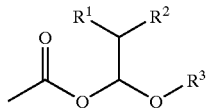

(IIa)

wherein R¹, R² and R³ have the same significances as defined above, respectively.

[6] A protective agent of a hydroxyl group comprising an alkenyl ether represented by the general formula (I)

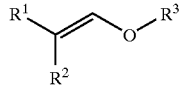

(I)

wherein R¹, R² and R³ have the same significances as defined above, respectively.

Hereinafter, the alkenyl ether represented by the general formula (I) may also be referred to as compound (I). Further, the compound having a group represented by the general formula (II) may also be referred to as compound (II).

[7] A chemical amplification type resist composition comprising an ether compound having a group represented by the general formula (II)

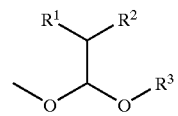

(II)

wherein R¹, R² and R³ have the same significances as defined above, respectively, and a photo acid generating agent.

[8] The chemical amplification type resist composition according to the above [7] wherein the ether compound having a group represented by the general formula (II) is a vinyl polymer having a structural unit represented by the general formula (III)

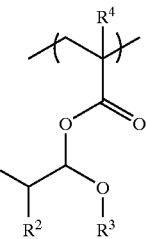

(III)

wherein R¹, R² and R³ have the same significances as defined above, respectively, and R⁴ represents a hydrogen atom or lower alkyl.

[9] The chemical amplification type resist composition according to the above [8] wherein number average molecular weight of the vinyl polymer having a structural unit represented by the general formula (III) is 1000 to 100000.

Hereinafter, the alkenyl ether represented by the general formula (I) may also be referred to as compound (I), whilst the ether compound having a group represented by the general formula (II) may also be referred to as compound (II).

In the definition of each group in the general formulae, the alkyl represents for example, straight chain or branched alkyl having 1 to 18 carbon atom(s), and specific examples thereof include methyl, ethyl, propyl, isopropyl, butyl, isobutyl, sec-butyl, tert-butyl, pentyl, hexyl, heptyl, octyl, nonyl, decyl, dodecyl, octadecyl and the like. Among them, alkyl having 1 to 6 carbon atom(s) is preferred, and alkyl having 1 to 3 carbon atom(s) is more preferred.

The lower alkyl represents for example, straight chain or branched alkyl having 1 to 6 carbon atom(s), and specific examples thereof include methyl, ethyl, propyl, isopropyl, butyl, isobutyl, sec-butyl, tert-butyl, pentyl, hexyl and the like.

Examples of the cycloalkyl formed by R¹ and R² together with an adjacent carbon atom include e.g., cycloalkyl having 3 to 8 carbon atoms, and specific examples thereof include cyclopropyl, cyclobutyl, cyclopentyl, cyclohexyl, cycloheptyl, cyclooctyl and the like.

Examples of the aryl include e.g., phenyl, naphthyl and the like.

Examples of the aralkyl include e.g., aralkyl having 7 to 15 carbon atoms, and specific examples thereof include benzyl, phenethyl, naphthylmethyl, naphthylethyl and the like.

Examples of the substituent of the alkyl include e.g., alkoxy, alkanoyl, cyano, nitro, halogen, alkoxycarbonyl and the like.

The alkyl moiety of the alkoxy and alkoxycarbonyl includes similar ones exemplified for the alkyl as described above.

Examples of the alkanoyl include e.g., straight chain or branched alkanoyl having 1 to 7 carbon atom(s), and specific examples thereof include formyl, acetyl, propionyl, butyryl, isobutyryl, valeryl, isovaleryl, pivaloyl, hexanoyl, heptanoyl and the like.

Examples of the halogen include each atom of fluorine, chlorine, bromine and iodine.

Examples of the substituent of the aryl and aralkyl include e.g., alkyl, alkoxy, alkanoyl, cyano, nitro, halogen, alkoxycarbonyl and the like.

Examples of the alkyl, alkoxy, alkanoyl, halogen and alkoxycarbonyl include similar ones as described above, respectively.

(1) Regarding Process for Producing Compound (II):

In this application, examples of the compound having a hydroxyl group include e.g., alcohols, phenols, compounds having a carboxyl group, and the like. Among them, compounds having a carboxyl group are preferred.

In the compound (I), it is preferred that all of the $R^1$, $R^2$ and $R^3$ are alkyl.

Specific example of the compound (I) include e.g., 1-methoxy-2-methylpropene, 1-ethoxy-2-methylpropene, 1-propoxy-2-methylpropene, 1-isopropoxy-2-methylpropene, 1-butoxy-2-methylpropene, 1-isobutoxy-2-propene, 1-(tert-butoxy)-2-methylpropene, 1-pentyloxy-2-methylpropene, 1-isopentyloxy-2-methylpropene, 1-neopentyloxy-2-methylpropene, 1-(tert-pentyloxy)-2-methylpropene, 1-hexyloxy-2-methylpropene, 1-isohexyloxy-2-methylpropene, 1-(2-ethylhexyl)-2-methylpropene, 1-heptyloxy-2-methylpropene, 1-octyloxy-2-methylpropene, 1-nonyloxy-2-methylpropene, 1-decanyloxy-2-methylpropene, 1-dodecanyloxy-2-methylpropene, 1-octadecanyloxy-2-methylpropene, 1-methoxy-2-methyl-1-butene, 1-ethoxy-2-methyl-1-butene, 1-propoxy-2-methyl-1-butene, 1-isopropoxy-2-methyl-1-butene, 1-butoxy-2-methyl-1-butene, 1-isobutoxy-2-methyl-1-butene, 1-(tert-butoxy)-2-methyl-1-butene, 1-pentyloxy-2-methyl-1-butene, 1-isopentyloxy-2-methyl-1-butene, 1-neopentyloxy-2-methyl-1-butene, 1-(tert-pentyloxy)-2-methyl-1-butene, 1-hexyloxy-2-methyl-1-butene, 1-isohexyloxy-2-methyl-1-butene, 1-(2-ethylhexyl)-2-methyl-1-butene, 1-heptyloxy-2-methyl-1-butene, 1-octyloxy-2-methyl-1-butene, 1-nonyloxy-2-methyl-1-butene, 1-decanyloxy-2-methyl-1-butene, 1-dodecanyloxy-2-methyl-1-butene, 1-octadecanyloxy-2-methyl-1-butene, 1-methoxy-2-ethyl-1-butene, 1-ethoxy-2-ethyl-1-butene, 1-propoxy-2-ethyl-1-butene, 1-isopropoxy-2-ethyl-1-butene, 1-butoxy-2-ethyl-1-butene, 1-isobutoxy-2-ethyl-1-butene, 1-(tert-butoxy)-2-ethyl-1-butene, 1-pentyloxy-2-ethyl-1-butene, 1-isopentyloxy-2-ethyl-1-butene, 1-neopentyloxy-2-ethyl-1-butene, 1-(tert-pentyloxy)-2-ethyl-1-butene, 1-hexyloxy-2-ethyl-1-butene, 1-isohexyloxy-2-ethyl-1-butene, 1-(2-ethylhexyl)-2-ethyl-1-butene, 1-heptyloxy-2-ethyl-1-butene, 1-octyloxy-2-ethyl-1-butene, 1-nonyloxy-2-ethyl-1-butene, 1-decanyloxy-2-ethyl-1-butene, 1-dodecanyloxy-2-ethyl-1-butene, 1-octadecanyloxy-2-ethyl-1-butene, 1-(2-methoxyethoxy)-2-methylpropene, 1-(2-ethoxyethoxy)-2-methylpropene, 1-(2-butoxyethoxy)-2-methyl propene, 1-(2-methoxyethoxy)-2-methyl-1-butene, 1-(2-ethoxyethoxy)-2-methyl-1-butene, 1-(2-butoxyethoxy)-2-methyl-1-butene, 1-(2-methoxyethoxy)-2-ethyl-1-butene, 1-(2-ethoxyethoxy)-2-ethyl-1-butene, 1-(2-butoxyethoxy)-2-ethyl-1-butene and the like. Among them, 1-propoxy-2-methylpropene is preferably used.

The compound (I) for use may be one, or two or more types.

The compound having a carboxyl group may be any saturated or unsaturated compound, and examples thereof include e.g., monocarboxylic acids such as formic acid, acetic acid, propionic acid, propiolic acid, butyric acid, isobutyric acid, hexanoic acid, heptanoic acid, octylic acid, nonanoic acid, isononanoic acid, decanoic acid, dodecanoic acid, stearic acid, benzoic acid, cinnamic acid, 2-naphthoic acid, nicotinic acid, isonicotinic acid, linseed oil fatty acid, tall oil fatty acid, soybean oil fatty acid and dehydrated castor oil fatty acid; multivalent carboxylic acids such as succinic acid, glutaric acid, adipic acid, azelaic acid, sebacylic acid, dodecane dioic acid, compounds having a decamethylene dicarboxyl group, phthalic acid, maleic acid, trimellitic acid, pyromellitic acid, tetrahydrophthalic acid, hexahydrophthalic acid and methylhexahydrophthalic acid; hydroxycarboxylic acids such as lactic acid, citric acid, hydroxypivalic acid, 12-hydroxystearic acid and malic acid; α,β-unsaturated monomers comprising a carboxyl group such as acrylic acid, methacrylic acid, itaconic acid, mesaconic acid, maleic acid and fumaric acid; as well as polymer compounds such as epoxy resins, alkyd resins and polyester resins comprising a carboxyl group in which the aforementioned polyvalent carboxylic acid is used as a material; vinyl copolymers comprising a carboxyl group in which the aforementioned α,β-unsaturated monomer comprising a carboxyl group is copolymerized with other α,β-unsaturated monomer; and the like. The α,β-unsaturated monomer comprising a carboxyl group or vinyl copolymer comprising a carboxyl group is preferably used.

Examples of alcohol include e.g., monoalcohols such as methanol, ethanol, propanol, isopropyl alcohol, n-butanol, isobutanol, sec-butyl alcohol, pentanol, hexanol, heptanol, octanol, nonanol, decanol and benzyl alcohol; and polyhydric alcohols such as ethylene glycol, 1,3-propylene glycol, 1,2-propylene glycol, 1,4-butanediol, 1,3-butanediol, 1,5-pentanediol, 3-methyl-1,5-pentanediol, 1,6-hexanediol, 1,8-octanediol, 2,4-diethyl-1,5-pentanediol, 2-butyl-2-ethyl-1,3-propanediol, 2,2-diethyl-1,3-propanediol, dodecanediol, neopentyl glycol, trimethylol propane, pentaerythritol, dipentaerythritol and glycerin.

Examples of phenols include low molecular weight phenol compounds such as phenol, resorcinol, hydroquinone, pyrocatechol, bisphenol A, dihydroxydiphenylmethane (bisphenol F), bisphenol S, tetrabromobisphenol A, 1,3-bis (4-hydroxyphenyl) cyclohexane, 4,4'-dihydroxy-3,3'-dimethyldiphenylmethane, 4,4'-dihydroxybenzophenone, tris(4-hydroxyphenyl)methane, bis(4-hydroxyphenyl)ether, novolac phenol, novolac cresol, bis(3,5-dimethyl-4-hydroxyphenyl)sulfone, bis(4-hydroxyphenyl)sulfone and hydroxystyrene; and copolymers in which any of phenol novolac resins, cresol novolac resins, and hydroxystyrene is copolymerized with other copolymerizable vinyl monomer. The copolymer in which phenol novolac resin, cresol novolac resin, or hydroxystyrene is copolymerized with other copolymerizable vinyl monomer is preferably used.

Among the processes for producing of the present invention, the process for the producing of an ether compound (hemiacetal ester) having a group represented by the general formula (IIa)

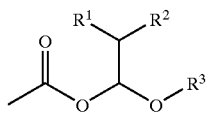

(IIa)

wherein $R^1$, $R^2$ and $R^3$ have the same significances as defined above, respectively, by allowing a compound having a carboxyl group to a reaction with an alkenyl ether represented by the general formula (I) is preferred.

In accordance with the process for producing of the present invention, equivalence ratio (molar ratio) of the compound having a hydroxyl group and the compound (I) is preferably 1:0.9 to 1:2, still preferably 1:0.9 to 1:1.5 and even more preferably 1:1 to 1:1.2. The reaction temperature is preferably 0 to 150° C., still preferably 0 to 100° C., and even more preferably 0 to 50° C.

In accordance with the process for producing of the present invention, it is preferred that an acid catalyst is used for the purpose of promoting the reaction. The acid catalyst is not particularly limited, and examples thereof include, inorganic acids such as hydrochloric acid, sulfuric acid, nitric acid and phosphoric acid; and organic acids such as p-toluenesulfonic acid. Among them, p-toluenesulfonic acid is preferred. The acid catalyst for use may be one, or two or more types. Although the amount of the acid catalyst to be added is not particularly limited, it is preferably used in amount of 0.0001 to 0.5 equivalent (molar ratio), more preferably 0.0001 to 0.1 equivalent on the basis of the compound having a hydroxyl group which shall be a material. In the process for producing of the present invention, the desired substance can be produced in a high yield with less side reaction even though any acid catalyst is employed.

In addition, an organic solvent may be used as needed. Examples of the organic solvent include, hydrocarbons solvents such as hexane, toluene and xylene; ethers solvents such as dioxane and tetrahydrofuran; ketones solvents such as acetone, methylethylketone and methylisobutylketone. One, or two or more kinds of the solvent may be used.

Introduction of a group derived from the compound (I) to a compound having a hydroxyl group and desorption from the compound (II) can be readily carried out, and the compound (I) can also be used as a protective agent of a hydroxyl group in organic syntheses.

(2) Regarding Step for Desorbing Group Derived from Compound (I), from Compound (II):

The group derived from the compound (I) in the compound (II) is desorbed from the compound (II) by a heat treatment or a treatment with an acid or the like. Upon the heat treatment or a treatment with an acid, an organic solvent may be used. Such an organic solvent may be similar ones as described above.

When desorption of the group derived from the compound (I) is conducted by a heat treatment, it is preferably executed at 160 to 200° C.

Further, when desorption of the group derived from the compound (I) is conducted by an acid treatment, examples of the acid for use include sulfuric acid, hydrochloric acid, p-toluenesulfonic acid and the like. Among them, p-toluenesulfonic acid is preferred. The acid is preferably used in an amount of 0.01 to 50 equivalent (molar ratio) on the basis of the compound (II). The temperature for the acid treatment is preferably 80 to 160° C. Upon the acid treatment, water may be added, and the amount of water which may be used is preferably 0.1 to 100% by weight on the basis of the compound (II). Moreover, when the addition of water is executed, the temperature in the acid treatment is preferably 20 to 80° C. Further, a photo acid generating agent may be used instead of the acid, and thus the group derived from the compound (I) in the compound (II) may be desorbed from the compound (II) by the acid generated upon irradiation of the light [In instances where a photo acid generating agent is used, the photo acid generating agent can be used similarly to the case in which the compound (II) is employed for use in a chemical amplification type resist composition as described herein below]. Additionally, a mode in which a group derived from the compound (I) is introduced into all of the multiple hydroxyl groups as described above, and a part thereof is subjected to desorption is also included in the concept of the process of the protection of the present invention.

As described hitherto, since introduction of a group derived from the compound (I) to a compound having a hydroxyl group, and desorption from the compound (II) can be readily carried out, the compound (II) can be used as a constitutive component of a chemical amplification type resist composition or the like.

(3) Regarding Chemical Amplification Type Resist Composition of the Present Invention:

Next, the chemical amplification type resist composition of the present invention is explained. The chemical amplification type resist composition of the present invention contains the compound (II) and a photo acid generating agent, however, the order of addition, method for mixing and the like of the compound (II) and the photo acid generating agent upon preparing the composition are not particularly limited.

When the compound (II) is used in a chemical amplification type resist composition, the compound (II) is preferably a polymer having a group represented by the general formula (II) (hereinafter, may be referred to as base polymer) and is more preferably a vinyl polymer having a group represented by the general formula (II). Among them, a vinyl polymer having a structural unit represented by the general formula (III) [hereinafter, may be referred to as polymer (III)] is more preferred, and still more preferred is a vinyl copolymer having a structural unit represented by the general formula (III). In the polymer (III), $R^4$ is preferably a hydrogen atom or methyl. Weight average molecular weight of the base polymer is preferably 1000 to 100000, and more preferably 1000 to 50000. The base polymer can be produced through for example, polymerizing a corresponding vinyl monomer by any of known methods (Japanese Published Unexamined Patent Application No. 59324/97 and 62190/95 and the like), or the modified method thereof.

The chemical amplification type resist composition of the present invention is preferably coated on a wafer after dissolving or dispersing in an organic solvent (a hydrocarbons solvent such as hexane, toluene or xylene; an ethers solvent such as dioxane or tetrahydrofuran; a ketones solvent such as acetone, methylethylketone or methylisobutylketone; an acetic acid ester such as ethyl acetate or propylene glycol monomethyl ether acetate; and the like). In this instance, the organic solvent is preferably used in an amount of 0.5 to 100 times by weight on the basis of the compound (II).

Thereafter, a heating step-(prebaking step) is conducted in order to evaporate the organic solvent on this wafer. The heating temperature in the prebaking step is preferably 80 to 130° C. The compound (II) is excellent in heat resistance, and thus is hardly decomposed at the heating temperature as described above. On the wafer after evaporating the organic solvent is irradiated an excimer laser (for example, KrF excimer laser) from an exposing apparatus. An acid is generated at the irradiated part by decomposition of the photo acid generating agent. Accordingly, a hydroxyl group is reproduced at the irradiated part. Furthermore, the compound with a hydroxyl group reproduced is washed away by an alkaline solution upon development to give a positive type resist.

Examples of the photo acid generating agent which may be used include onium salt compounds, sulfone compounds, sulfonic acid ester compounds, diazosulfone compounds, disulfonylmethane compounds, sulfoneimide compounds, nitrobenzyl compounds, naphthoquinone diazide compound and the like.

Examples of the onium salt compound include, bis(4-tert-butylphenyl)iodonium trifluoromethanesulfonate, bis(4-tert-butylphenyl)iodonium nonafluorobutanesulfonate, bis(4-tertbutylphenyl)iodonium-2-trifluoromethyl benzenesulfonate, bis(4-tert-butylphenyl)iodonium-10-camphorsulfonate, bis(4-tert-butylphenyl)iodonium-p-toluenesulfonate, diphenyliodonium trifluoromethanesulfonate, diphenyliodonium nonafluorobutanesulfonate, diphenyliodonium-2-trifluoromethyl benzenesulfonate, diphenyliodonium-10-camphorsulfonate, diphenyliodonium-p-toluenesulfonate, triphenylsulfonium trifluoromethanesulfonate, triphenylsulfonium nonafluorobutanesulfonate, triphenylsulfonium-2-trifluoromethyl benzenesulfonate, triphenylsulfonium-10-camphorsulfonate, triphenylsulfonium-p-toluenesulfonate, 4-tert-butylphenyldiphenylsulfonium trifluoromethanesulfonate, 4-tert-butylphenyldiphenylsulfonium nonafluorobutanesulfonate, 4-tert-butylphenyldiphenylsulfonium-2-trifluoromethyl benzenesulfonate, 4-tert-butylphenyldiphenylsulfonium-10-camphorsulfonate, 4-tert-butylphenyldiphenylsulfonium-p-toluenesulfonate, 4-tert-butoxyphenyldiphenylsulfonium trifluoromethanesulfonate, 4-tert-butoxyphenyldiphenylsulfonium nonafluorobutanesulfonate, 4-tert-butoxyphenyldiphenylsulfonium-2-trifluoromethyl benzenesulfonate, 4-tert-butoxyphenyldiphenylsulfonium-10-camphorsulfonate, 4-tert-butoxyphenyldiphenylsulfonium-p-toluenesulfonate and the like.

Examples of the sulfone compound include β-ketosulfone, β-sulfonylsulfone and α-diazo compounds thereof and the like.

Examples of the sulfonic acid ester compound include e.g., benzoin tosilate, pyrogallol tristrifluorosulfonate, pyrogallol methanesulfonic acid triester, nitrobenzyl-9,10-diethoxyanthracene-2-sulfonate, α-methylolbenzoisocyanate, α-methylolbenzoin octanesulfonate, α-methylolbenzoin trifluoromethanesulfonate, α-methylolbenzoin dodecylsulfonate and the like.

Examples of the sulfoneimide compound include, N-(trifluoromethylsulfonyloxy) succinimide, N-(trifluoromethylsulfonyloxy)phthalimide, N-(trifluoromethylsulfonyloxy)diphenylmaleimide, N-(trifluoromethylsulfonyloxy)bicyclo[2.2.1]hept-5-ene-2,3-dicarboximide, N-(trifluoromethylsulfonyloxy)-7-oxabicyclo[2.2.1]hept-5-ene-2,3-dicarboximide, N-(trifluoromethylsulfonyloxy)bicyclo[2.2.1]heptane-5,6-dioxy-2,3-dicarboximide, N-(trifluoromethylsulfonyloxy)naphthylimide, N-(camphorsulfonyloxy) succinimide, N-(camphorsulfonyloxy)phthalimide, N-(camphorsulfonyloxy)diphenylmaleimide, N-(camphorsulfonyloxy)bicyclo[2.2.1]hept-5-ene-2,3-dicarboximide, N-(camphorsulfonyloxy)-7-oxabicyclo[2.2.1]hept-5-ene-2,3-dicarboximide, N-(camphorsulfonyloxy)bicyclo[2.2.1]heptane-5,6-dioxy-2,3-dicarboximide, N-(camphorsulfonyloxy)naphthylimide, N-(4-methylphenylsulfonyloxy)succinimide, N-(4-methylphenylsulfonyloxy)phthalimide, N-(4-methylphenylsulfonyloxy)diphenylmaleimide, N-(4-methylphenylsulfonyloxy)bicyclo[2.2.1]hept-5-ene-2,3-dicarboximide, N-(4-methylphenylsulfonyloxy)-7-oxabicyclo[2.2.1]hept-5-ene-2,3-dicarboximide, N-4-methylphenylsulfonyloxy)bicyclo[2.2.1]heptane-5,6-dioxy-2,3-dicarboximide, N-(4-methylphenylsulfonyloxy)naphthylimide, N-(2-trifluoromethylphenylsulfonyloxy)succinimide, N-(2-trifluoromethylphenylsulfonyloxy)phthalimide, N-(2-trifluoromethylphenylsulfonyloxy)diphenylmaleimide, N-(2-trifluoromethylphenylsulfonyloxy)bicyclo[2.2.1]hept-5-ene-2,3-dicarboximide, N-(2-trifluoromethylphenylsulfonyloxy)-7-oxabicyclo[2.2.1]hept-5-ene-2,3-dicarboximide, N-(2-trifluoromethylphenylsulfonyloxy) bicyclo[2.2.1]heptane-5,6-dioxy-2,3-dicarboximide, N-(2-trifluoromethylphenylsulfonyloxy)naphthylimide, N-(4-fluorophenylsulfonyloxy)succinimide, N-(4-fluorophenylsulfonyloxy)phthalimide, N-(4-fluorophenylsulfonyloxy)diphenylmaleimide, N-(4-fluorophenylsulfonyloxy)bicyclo[2.2.1]hept-5-ene-2,3-dicarboximide, N-(4-fluorophenylsulfonyloxy)bicyclo[2.2.1]heptane-5,6-dioxy-2,3-dicarboximide, N-(4-fluorophenylsulfonyloxy)naphthylimide and the like.

The amount of the photo acid generating agent to be included is preferably 0.01 to 50 parts by weight, more preferably 0.1 to 30 parts by weight, and still more preferably 0.5 to 25 parts by weight per 100 parts by weight of the compound (II).

The chemical amplification type resist composition of the present invention is excellent in stability during the prebaking step and storage stability in a long period of time, and has satisfactory lithography characteristics.

BEST MODE FOR CARRYING OUT THE INVENTION

Conversion ratio of the material and selection ratio to the desired substance in Examples and Comparative Examples were obtained through the determination by a gas chromatographic analysis. In the determination, GC-14A manufactured by Shimadzu Corporation was used, with the column for use being INNOWAX (length: 30 m, diameter: 0.25 mm) manufactured by Hewlett-Packard Co. Injection temperature of the sample and the detector temperature were both 200° C., and the analysis was made by elevating the column temperature from 50° C. to 200° C. at 10° C./min. Determination after the gas chromatographic analysis was carried out by an absolute calibration method.

For the differential thermal scale analysis, TG/TDA6200 manufactured by Seiko Instruments, Inc., was used, and the measurement was carried out under a nitrogen atmosphere through elevating the temperature from 40° C. to 400° C. at 10° C./min.

Measurement of the acid value was performed according to JIS K0070.

In addition, number average molecular weight (Mn) and molecular weight distribution (Mw/Mn: weight average molecular weight/number average molecular weight) of the polymer in the following Examples was measured by a gel permeation chromatography under following condition.

Column: TSKgel Super HM-M (2 columns) and HM-H (1 column) [all manufactured by Tosoh Corporation] were serially connected.

Column retention temperature: 40° C.
Detector: RI
Developing solvent: tetrahydrofuran (flow rate: 0.5 ml/min)
Standard reference: polystyrene

EXAMPLE 1

Synthesis of Monomer

Methacrylic acid in an amount of 45.7 g and 1-propoxy-2-methylpropene in an amount of 121.4 g were subjected to a reaction in the presence of 0.02 mol % p-toluenesulfonic acid monohydrate on the basis of methacrylic acid at room temperature for 1.5 hours. The conversion ratio of methacrylic acid 99% or greater, with the selection ratio to 1-propoxy-2-methylpropyl methacrylate being 99% or greater. After neutralizing the reaction mixture with 1% aqueous solution of sodium carbonate, 105 g of 1-propoxy-2-methylpropyl methacrylate was obtained through vacuum concentration of the organic layer yielded from the liquid separation.
Identification data
$^1$H-NMR spectrum (400 MHz)
Equipment for the measurement: JEOL, Ltd. GSX-400
Solvent for the measurement; chloroform-d
δ(ppm) 6.18–6.16 (m, 1H)
5.68 (d, J=5.1 Hz, 1H)
5.61–5.58 (m, 1H)
3.62 (dt, J=9.5, 6.6 Hz, 1H)
3.45 (dt, J=9.5, 6.6 Hz, 1H)
1.98–1.95 (m, 4H)
1.63–1.53 (m, 2H)
0.97 (d, J=6.8 Hz, 3H)
0.93 (d, J=6.8 Hz, 3H)
0.92 (t, J=7.3 Hz, 3H)

EXAMPLE 2

Synthesis of Monomer

Methacrylic acid in an amount of 1.7 g and 1-methoxy-2-methylpropene in an amount of 2.5 g were subjected to a reaction in the presence of 0.02 mol % p-toluenesulfonic acid monohydrate at room temperature for 2.5 hours. The conversion ratio of methacrylic acid was then 90% or greater, with the selection ratio to 1-methoxy-2-methylpropyl methacrylate being 99% or greater. After neutralizing the reaction mixture with 5% aqueous solution of sodium carbonate, 2.7 g of 1-methoxy-2-methylpropyl methacrylate was obtained through vacuum concentration of the organic layer yielded from the liquid separation.
Identification data
$^1$H-NMR spectrum (400 MHz)
Equipment for the measurement: JEOL, Ltd. GSX-400
Solvent for the measurement; chloroform-d
δ(ppm) 6.19–6.17 (m, 1H)
5.62–5.60 (m, 2H)
3.42 (s, 3H)
1.99–1.96 (m, 4H)
0.96 (d, J=6.8 Hz, 3H)
0.95 (d, J=6.8 Hz, 3H)

EXAMPLE 3

Synthesis of Monomer

Methacrylic acid in an amount of 48.2 g and 1-ethoxy-2-methylpropene in an amount of 80.0 g were subjected to a reaction in the presence of 0.02 mol % p-toluenesulfonic acid monohydrate at room temperature for 3 hours. The conversion ratio of methacrylic acid was 90% or greater, with the selection ratio to 1-ethoxy-2-methylpropyl methacrylate being 99% or greater. After neutralizing the reaction mixture with 5% aqueous solution of sodium carbonate, 83.6 g of 1-ethoxy-2-methylpropyl methacrylate was obtained through vacuum concentration of the organic layer yielded from the liquid separation.
$^1$H-NMR spectrum (400 MHz)
Equipment for the measurement: JEOL, Ltd. GSX-400
Solvent for the measurement; chloroform-d
δ(ppm) 6.18–6.16 (m, 1H)
5.69 (d, J=5.1 Hz, 1H)
5.61–5.59 (m, 1H)
3.73 (dq, J=9.8, 7.1 Hz, 1H)
3.56 (dq, J=9.8, 7.1 Hz, 1H)
2.00–1.92 (m, 4H)
1.20 (t, J=7.1 Hz, 3H)
0.97 (d, J=6.8 Hz, 3H)
0.94 (d, J=6.8 Hz, 3H)

EXAMPLE 4

Synthesis of Monomer

Methacrylic acid in an amount of 53.2 g and 1-ethoxy-2-ethyl-1-butene in an amount of 159 g were subjected to a reaction in the presence of 0.02 mol % p-toluenesulfonic acid monohydrate at room temperature for 3.5 hours. The conversion ratio of methacrylic acid was 75%, with the selection ratio to 1-ethoxy-2-ethylbutyl methacrylate being 99% or greater. After neutralizing the reaction mixture with 5% aqueous solution of sodium carbonate, 100 g of 1-ethoxy-2-ethylbutyl methacrylate was obtained through vacuum concentration of the organic layer yielded from the liquid separation.
Identification data
$^1$H-NMR spectrum (400 MHz)
Equipment for the measurement: JEOL, Ltd. GSX-400
Solvent for the measurement; chloroform-d
δ(ppm) 6.17–6.16 (m, 1H)
5.90 (d, J=4.4 Hz, 1H)
5.59–5.60 (m, 1H)
3.75–3.68 (m, 1H)
3.60–3.52 (m, 1H)
1.98–1.96 (m, 3H)
1.62–1.30 (m, 5H)
1.21 (t, J=7.1 Hz, 3H)
0.92 (t, J=7.5 Hz, 3H)
0.91 (t, J=7.5 Hz, 3H)

EXAMPLE 5

Synthesis of Polymer

1-Propoxy-2-methylpropyl methacrylate obtained in Example 1 was heated in an amount of 10.0 g in 23 g of chlorobenzene, in the presence of 3 mol % AIBN at 70° C. for 5 hours. The reaction mixture was added dropwise into methanol to precipitate poly-(1-propoxy-2-methylpropyl methacrylate). The precipitates were separated by filtration, and thus 7.9 g of poly-(1-propoxy-2-methylpropyl methacrylate) was obtained by vacuum drying. As a result of differential thermal scale analysis conducted for this polymer, the temperature for initiation of decomposition was 153° C. In addition, this polymer had Mn of 9682, and Mw/Mn of 2.2.

EXAMPLE 6

Synthesis of Polymer

1-Methoxy-2-methylpropyl methacrylate obtained in Example 2 was heated in an amount of 4.30 g in 11.5 g of chlorobenzene, in the presence of 6 mol % AIBN at 70 to 80° C. for 7 hours. The reaction mixture was added dropwise into 120 g of methanol, and thus 1.63 g of poly-(1-methoxy-2-methylpropyl methacrylate) was obtained through separation of the precipitated solid. As a result of differential thermal scale analysis conducted for this polymer, the temperature for initiation of decomposition was 162° C. In addition, this polymer had Mn of 8830, and Mw/Mn of 2.1.

EXAMPLE 7

Synthesis of Polymer

1-Ethoxy-2-methylpropyl methacrylate obtained in Example 3 was heated in an amount of 5.00 g in 13.2 g of chlorobenzene, in the presence of 6 mol % AIBN at 75° C. for 5 hours. The reaction mixture was added dropwise into 300 g of methanol, and thus 3.80 g of poly-(1-ethoxy-2-methylpropyl methacrylate) was obtained through separation of the precipitated solid. As a result of differential thermal scale analysis conducted for this polymer, the temperature for initiation of decomposition was 157° C. In addition, this polymer had Mn of 6533, and Mw/Mn of 1.9.

EXAMPLE 8

Synthesis of Polymer

1-Ethoxy-2-ethylbutyl methacrylate obtained in Example 4 was heated in an amount of 5.00 g in 13.2 g of chlorobenzene, in the presence of 6 mol % AIBN at 75° C. for 5 hours. The reaction mixture was added dropwise into 300 g of methanol, and 4.3 g of poly-(1-ethoxy-2-ethylbutyl methacrylate) was obtained through separation of the precipitated solid. As a result of differential thermal scale analysis conducted for this polymer, the temperature for initiation of decomposition was 148° C. In addition, this polymer had Mn of 6239, and Mw/Mn of 2.3.

COMPARATIVE EXAMPLE 1

Synthesis of Monomer

To a mixture of 1.00 g of methacrylic acid and 0.836 g of ethyl vinyl ether was added 2 mg of p-toluenesulfonic acid monohydrate, and a reaction was allowed at room temperature for 1 hour. The conversion ratio of methacrylic acid was 82%, with the conversion ratio of ethyl vinyl ether of 94%. Accordingly, 1-ethoxyethyl methacrylate was obtained with the reaction yield of 80% and the selection ratio to ethyl vinyl ether of 85%, and a polymer of ethyl vinyl ether was produced.

TEST EXAMPLE 1

Storage Stability of Monomer

1-Propoxy-2-methylpropyl methacrylate obtained in Example 1 in an amount of 10 g and 1-ethoxyethyl methacrylate obtained in Comparative Example 1 in an amount of 10 g were packed in a 20 ml glass vial, respectively. After sealing, the vials were stored in a thermoregulated bath at 40° C. Measurement of the acid value was performed before the test, and on 15 days and 30 days after the test. The results are shown in Table 1.

TABLE 1

|  | Acid value (mg KOH/g) | | |
| --- | --- | --- | --- |
|  | Before test | 15 days | 30 days |
| Monomer produced in Example 1 | 0.050 | 0.051 | 0.052 |
| Monomer produced in Comparative Example 1 | 0.110 | 0.228 | 0.375 |

From Table 1, it was confirmed that the monomer produced in Example 1 was more excellent in storage stability in comparison with the monomer produced in Comparative Example 1.

EXAMPLE 9

Poly-(1-Propoxy-2-methylpropyl methacrylate) obtained in Example 5 in an amount of 3.0 g and 15 mg of p-toluenesulfonic acid monohydrate were dissolved in 36.2 g of toluene. After stirring the mixture at room temperature for 10 minutes, toluene was distilled out under a reduced pressure of 0.92 kPa with heating at 50° C. Resulting concentrated residue was heated under a reduced pressure of 0.92 kPa at 100° C. for 30 minutes and deprotection ratio was determined by measuring the acid value to give polymethacrylic acid with the deprotection ratio of 96%.

EXAMPLE 10

Propylene glycol monomethyl ether acetate in an amount of 30 g was charged in a 100 ml four necked flask equipped with a thermometer, a dropping funnel and a tube for introducing nitrogen, and the temperature was elevated up to 80° C. When the temperature became stable, a mixture of 4.6 g of 1-propoxy-2-methylpropyl methacrylate obtained in Example 1, 18.2 g of methyl methacrylate and 0.4 g of 2,2'-azobis(2-methylbutyronitrile) was thereto added dropwise over 2 hours under a nitrogen atmosphere. After completing the dropwise addition, the mixture was further subjected to aging at the same temperature for 3.5 hours, and cooled. Then, thus resulting polymer solution was added dropwise while stirring slowly in 1000 ml of hexane to effect purification by reprecipitation. Thus precipitated polymer was dissolved in acetone, and similar operation was repeated three times. The resultant-polymer was dried overnight by vacuum drying to give a white solid polymer. Furthermore, 20 g of thus obtained solid polymer was dissolved in 80 g of propylene glycol monomethyl ether acetate, and thereto was blended 1% by weight of diphenyliodonium trifluoromethanesulfonate (DPI-OTf) as a photo acid generating agent to give a propylene glycol monomethyl ether acetate solution of a chemical amplification type resist composition.

Styrene equivalent number average molecular weight of the polymer in the chemical amplification type resist composition was 10200.

TEST EXAMPLE 2

Evaluation of Chemical Amplification Type Resist Composition

Evaluation on sensitivity was performed under the following condition using the chemical amplification type resist composition obtained in Example 10.
(Conditions for Exposure and Development)
Prebaking step: 120° C.×5 min.
Exposure: low-pressure mercury lamp (254 nm) manufactured by Toshiba Corporation
Amount of exposure: 8 mJ/cm$^2$
Post exposure bake: 100° C.×2 min.
Developing fluid: 2.38% by weight aqueous tetramethylammonium hydroxide solution
When the resist pattern obtained under the conditions described above was observed with a scanning electron microscope, resolution of a 2 μm line and space pattern was ascertained with the line width as defined.

EXAMPLE 11

Protection of Phenolic Hydroxyl Group

In 5.00 g of toluene were dissolved 1.00 g of phenol, 2.12 g of 1-ethoxy-2-methylpropene and 27 mg of a p-toluenesulfonic acid pyridinium salt, and a reaction was allowed at room temperature for 15 hours. After distilling toluene out from the reaction mixture under a reduced pressure, the concentrated residue was purified on a silica gel chromatography to give 1.40 g of 1-ethoxy-2-methylpropoxybenzene.
Identification data
$^1$H-NMR spectrum (400 MHz)
Equipment for the measurement: JEOL, Ltd. GSX-400
Solvent for the measurement; chloroform-d
δ(ppm) 7.30–7.22 (m, 2H)
7.08–6.95 (m, 3H)
4.99 (d, J=6.1 Hz, 1H)
3.75–3.67 (m, 1H)
3.54–3.47 (m, 1H)
2.35–2.07 (m, 1H)
1.17 (t, J=7.1 Hz, 3H)
1.01 (d, J=6.8 Hz, 6H)

INDUSTRIAL APPLICABILITY

According to the present invention, a process for producing an ether compound, which is useful for chemical amplification type resist compositions, synthetic intermediates of pharmaceuticals, paints, or the like, with less side reaction and in a high yield; a protective agent of a hydroxyl group, which can give a compound with a hydroxyl group protected that is excellent in thermostability; or the like can be provided.

The invention claimed is:

1. A process for producing an ether compound having a group represented by formula (II)

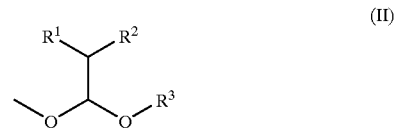

wherein R$^1$, R$^2$ and R$^3$ independently represent substituted or unsubstituted alkyl, substituted or unsubstituted aryl or substituted or unsubstituted aralkyl, or R$^1$ and R$^2$ form cycloalkyl together with an adjacent carbon atom, which comprises allowing a compound having a hydroxyl group to react with an alkenyl ether represented by the general formula (I)

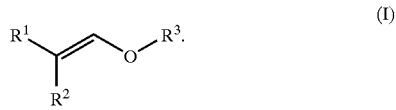

2. The process for producing according to claim 1 wherein the reaction is conducted in the presence of an acid catalyst.

3. A process for protecting a hydroxyl group which comprises allowing a compound having a hydroxyl group to react with an alkenyl ether represented by the general formula (I)

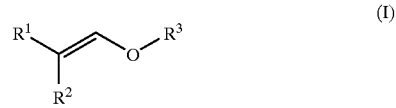

wherein R$^1$, R$^2$ and R$^3$ independently represent substituted or unsubstituted alkyl, substituted or unsubstituted aryl or substituted or unsubstituted aralkyl, or R$^1$ and R$^2$ form cycloalkyl together with an adjacent carbon atom to lead to an ether compound having a group represented by the general formula (II)

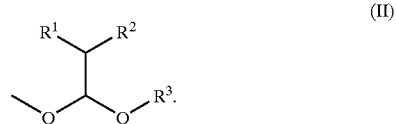

* * * * *

UNITED STATES PATENT AND TRADEMARK OFFICE
CERTIFICATE OF CORRECTION

PATENT NO. : 7,015,363 B2
APPLICATION NO. : 10/482111
DATED : March 21, 2006
INVENTOR(S) : Ikuo Shimizu et al.

It is certified that error appears in the above-identified patent and that said Letters Patent is hereby corrected as shown below:

TITLE PAGE AT (57) ABSTRACT

Line 2, "producing and the like, which enables the" should be deleted.

COLUMN 3

Line 31, "lead" should read --provide--.

COLUMN 5

Line 61, "2-methyl propene," should read --2-methylpropene,--.

COLUMN 6

Line 31, "other" should read --another--; and
Line 62, "other" should read --another--.

COLUMN 7

Line 16, "still" should read --more--;
Line 18, "still" should read --more--; and
Line 54, "be" should read --include--.

UNITED STATES PATENT AND TRADEMARK OFFICE
CERTIFICATE OF CORRECTION

PATENT NO. : 7,015,363 B2
APPLICATION NO. : 10/482111
DATED : March 21, 2006
INVENTOR(S) : Ikuo Shimizu et al.

It is certified that error appears in the above-identified patent and that said Letters Patent is hereby corrected as shown below:

COLUMN 16

Line 29, "producing according to claim 1" should read --producing an ether compound according to claim 1,--; and
Line 47, "an" should read --the--.

Signed and Sealed this

Eighth Day of August, 2006

JON W. DUDAS
*Director of the United States Patent and Trademark Office*